(12) United States Patent
Camp

(10) Patent No.: US 7,740,402 B2
(45) Date of Patent: Jun. 22, 2010

(54) FLUID DETECTOR

(75) Inventor: Philip George Camp, Taunton (GB)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 12/202,589

(22) Filed: Sep. 2, 2008

(65) Prior Publication Data

US 2009/0071243 A1 Mar. 19, 2009

(30) Foreign Application Priority Data

Sep. 14, 2007 (EP) .................................. 07116478

(51) Int. Cl.
*G01K 13/00* (2006.01)
*G01N 25/00* (2006.01)
(52) U.S. Cl. ........................ 374/45; 374/183; 374/148
(58) Field of Classification Search .................. 374/45, 374/43, 183, 148
See application file for complete search history.

(56) References Cited

U.S. PATENT DOCUMENTS

| 3,803,913 | A | | 4/1974 | Tracer |
| 4,043,196 | A | | 8/1977 | Trageser |
| 5,339,687 | A | * | 8/1994 | Gimson et al. ........... 73/204.19 |
| 6,681,625 | B1 | * | 1/2004 | Berkcan et al. .......... 73/204.23 |
| 7,013,714 | B2 | * | 3/2006 | Lin ............................ 73/54.42 |
| 2003/0225544 | A1 | | 12/2003 | Ismail et al. |
| 2007/0146149 | A1 | * | 6/2007 | Abe et al. ................... 340/622 |
| 2008/0066541 | A1 | * | 3/2008 | Burton ...................... 73/204.15 |

FOREIGN PATENT DOCUMENTS

| WO | WO 90/09567 A | 8/1990 |
| WO | WO 02/21055 A2 | 3/2002 |

OTHER PUBLICATIONS

Database WPI Week 1996. Thomson Scientific, London, GB. XP-0024793909, Jun. 7, 1996, XP-002473909.

* cited by examiner

*Primary Examiner*—Gail Verbitsky
*Assistant Examiner*—Mirellys Jagan
(74) *Attorney, Agent, or Firm*—Global Patent Operation; Mark A. Conklin

(57) ABSTRACT

A detector and a method for determining the presence of a fluid are disclosed. The detector comprises a probe having a thermistor with the probe being arranged to be exposed to a fluid and to allow thermal flow between the thermistor and the fluid, a temperature sensor for measuring the temperature of the thermistor and a controller. The controller is arranged to supply electrical power to the thermistor when it is below a predetermined temperature to heat it up and to turn off the supply of electrical power to the thermistor when it is at or above the predetermined temperature. The presence or identity of a fluid exposed to the probe is determined based on the proportion of time that power is supplied to the thermistor to maintain it substantially at the predetermined temperature. The ambient temperature of the fluid to which the probe is exposed may also be measured and electrical power may be supplied to the thermistor to keep it substantially at a predetermined temperature above the measured ambient temperature.

8 Claims, 4 Drawing Sheets

FIG. 1
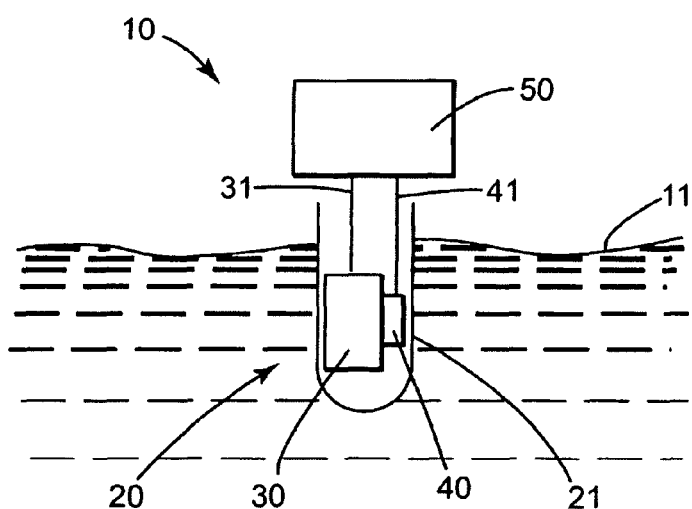
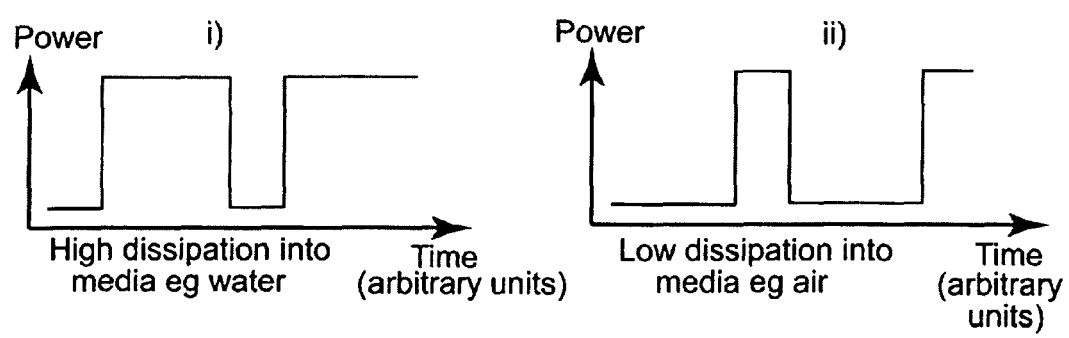
FIG. 2

FLUID DETECTOR

FIELD AND BACKGROUND OF THE INVENTION

This invention relates to detection of the presence of media, in particular fluids.

The detection of the presence of fluids has many applications. For example, domestic heating systems preferably have a sensor to detect whether or not liquid is present in the heat exchanger and whether or not it is flowing in order to confirm that the pump is running. Detectors are also employed in many other applications, such as engine coolant systems for vehicles and domestic appliances such as refrigerators, washing machines etc.

A fluid sensor may comprise a probe including one or more thermistors. The thermistors are preheated by applying a voltage from a heating circuit. When the probe is exposed to fluid, the fluid conducts heat away from the thermistor reducing its temperature. As the effective thermal conductivity of fluids such as air, oil, water and moving fluids such as moving water are different, the presence of each of these at the surface of the probe can be determined remotely by measuring the reduction in temperature of the thermistor. Such a flow sensor is disclosed in EP-A-1 647 813.

A thermistor may also be kept at a substantially constant predetermined target temperature. The constant predetermined target temperature may be at a set level above the surrounding ambient temperature, such as by 20 to 30° C. By measuring the power needed to keep the thermistor at the constant temperature, a rate of power dissipation into the surrounding media can be determined, and thus the presence/absence or nature of the fluid in which the thermistor is provided may be determined.

Electrical power is generally applied to a thermistor by a constant current source. When the thermistor is at the required predetermined temperature, a suitable resistance load is introduced into the circuit supplying electrical power to the thermistor so that the proportion of electrical power and thus heating of the thermistor is reduced to prevent it from heating up further, beyond the predetermined target temperature. However, the introduction of a resistance load wastes a considerable amount of power, especially if the detector is used for long periods of time or constantly.

It would be desirable to be able to reduce power consumption in a fluid detector.

SUMMARY OF THE INVENTION

According to a first aspect of the present invention there is provided a detector for determining the presence of a fluid, the detector comprising:
  a. a probe having a thermistor, the probe being arranged to be exposed to a fluid;
  b. a temperature sensor for measuring the temperature of the thermistor; and
  c. a controller for supplying electrical power to the thermistor when it is below a predetermined temperature to heat it up and to turn off the supply of electrical power to the thermistor when it is at or above the predetermined temperature, and to determine the presence of a fluid exposed to the probe in accordance with the proportion of time that power is supplied to the thermistor to maintain it substantially at the predetermined temperature.

Consequently, the controller is arranged to supply power intermittently to the probe to keep it at a substantially constant predetermined target temperature. As power is supplied intermittently or in a pulsed manner, overall power consumption is reduced.

By determining the proportion of time that power is supplied to the thermistor to keep it at the predetermined temperature, the identity or type of media in which the probe is provided may be determined as different fluids have different thermal capacities.

According to a second aspect of the present invention, there is provided a method of determining the presence of a fluid, the method comprising:
  a. exposing a probe including a thermistor to a fluid;
  b. measuring the temperature of the thermistor;
  c. controlling the supply of electrical power to the thermistor to keep it substantially at a predetermined temperature by supplying electrical power to the thermistor when it is below a predetermined temperature to heat it up and turning off the supply of electrical power to the thermistor when it is at or above the predetermined temperature; and
  d. determining the presence of a fluid in contact with the probe in accordance with the proportion of time that power is supplied to the thermistor.

BRIEF DESCRIPTION OF THE DRAWINGS

Embodiments of the present invention will now be described, by way of example only, with reference to the accompanying drawings in which:

FIG. 1 schematically shows a detector for determining the presence of a fluid;

FIG. 2 shows waveforms indicative of power supplied to a thermistor of a detector when exposed to i) water and ii) air;

DETAILED DESCRIPTION OF THE INVENTION

Figure 3:
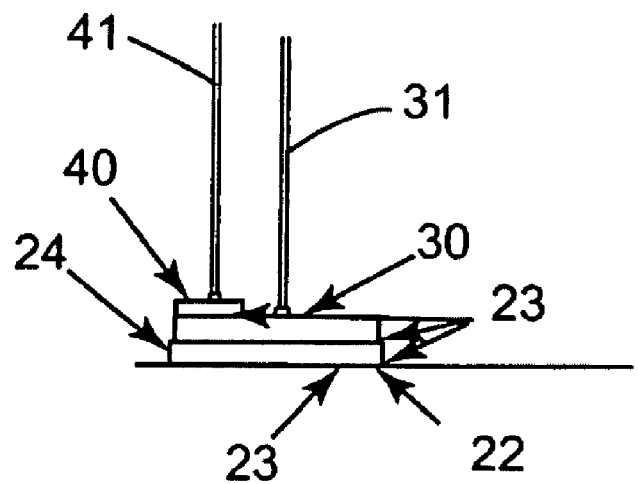
FIG. 3 shows a side view of the probe structure of an embodiment of the present invention.

FIG. 1 schematically shows a detector 10 of an embodiment of the present invention. The detector 10 comprises a probe 20 arranged to be exposed to a fluid 11. Any suitable fluid may be detected, such as gases, in particular air, and liquids, such as water and oil and/or moving fluids such as flowing air or water which have different thermal capacities when they are moving from when they are static.

The probe 20 includes a thermistor 30. The thermistor 30 is in good thermal contact with the fluid 11 via the outer surface 21 of the probe 20. Any suitable thermistor 30 may be used as is well known to those skilled in the art, provided that its resistance varies with temperature.

A temperature sensor 40 is provided within the probe to measure the temperature of the thermistor 30. In this example, the temperature sensor 40 is mounted on the thermistor 30.

The thermistor 30 and temperature sensor 40 are each electrically connected to a controller 50 via respective electrical connectors 31, 41. The controller 50 is arranged to keep the thermistor substantially at a predetermined target temperature during use. The controller 50 supplies electrical power to the thermistor to heat it up when it is below the predetermined temperature and turns off the supply of electrical power to the thermistor when it is at or above the predetermined temperature. The controller is also arranged to determine the presence of the fluid 11 to which the probe 20 is exposed in accordance with the proportion of time that power is supplied to the thermistor 30. This determination may be made by the controller 50 itself or by using a further device or controller associated with the detector 10. As well as determining the presence of a fluid in contact with the probe 20, the controller may also be arranged to determine the type of fluid such as air, water or oil and whether it is still or moving depending upon the proportion of time that power is supplied to the thermistor 30 to maintain it at the predetermined target temperature.

The controller may be implemented in any suitable way as will be appreciated by a person skilled in the art, such as by an electronic circuit, a microprocessor, a computer arrangement or a combination of these connected or associated together.

FIG. 2 illustrates two waveforms illustrating the turning on and off of power to the thermistor 30 over time. The first waveform labelled i) illustrates a relatively high dissipation of power into water 11. As can be seen, power is supplied to the thermistor 30 for a relatively large proportion of time because the fluid 11, in this example water, has a relatively high thermal conductivity.

In contrast, the second waveform of FIG. 2 labelled ii) illustrates an example in which the probe 20 is exposed to air. As can be seen, power is supplied to the thermistor 30 for a smaller proportion of time as air has a lower thermal conductivity than water and so the thermistor 30 only needs to be heated for a shorter period of time to keep it at the desired predetermined target temperature.

Exposure to different fluids 11 will require the supply of power to the thermistor 30 for different proportions of time. The detector may be calibrated with a number of known fluids to which the probe 20 may be exposed such that the proportion of time for which power will be supplied to the thermistor 30 for each fluid will be known. These known proportions of time may be stored in a memory or look-up table for example, correlated to the media to which they correspond such that when measurements are made during use, the measured proportion of time that power is supplied to the thermistor 30 may be used to determine the media to which the probe 20 is exposed.

As well as storing the proportions of time that power is supplied to the thermistor 30 corresponding to particular media, such as air, water and oil, the proportions of time for which power is supplied to the thermistor for fluids in different states, such as static or moving may also be stored.

FIG. 3 shows a side view of a portion of the probe 20 including the thermistor 30 and temperature sensor 40. In this example, the thermistor 30 is termed a self heated thermistor and the temperature sensor 40 is provided by a feedback thermistor in intimate thermal contact with the self heated thermistor 30. The feedback thermistor may be soldered directly to the self heated thermistor 30 as shown in FIG. 2. Alternatively, both thermistors 30, 40 may share the same ceramic chip. In the example of FIG. 2, the probe 20 has a stainless steel outer case 22, only a portion of which is shown in this view, with a sputtered solder layer on its inside surface. A metallised ceramic layer 24 such as $Al_2O_3$ or AlN is provided between the stainless steel case 22 and the self heated thermistor 30 which is soldered 23 to the metallised ceramic layer 24. The feedback thermistor 40 is soldered 23 to the self heated thermistor 30. The metallised ceramic layer 24 provides a small and consistent temperature gradient between the self heated thermistor 30 and the media 11 so that that different media may be precisely identified. As well as having a relatively high thermal conductivity, the metallised ceramic layer 24 also exhibits a relatively high dielectric value in order to electrically isolate the self heated thermistor 30 from the media 11.

Electrical connection is made with fine thermally resistive wires, 31, 41 to prevent unwanted heat loss. The thermistor sub-assembly may be coated with a protective resin.

The self heated thermistor 30 in this example is made from a metallised ceramic which has a relatively poor thermal conductivity. Consequently, the self heated thermistor 30 preferably has a surface area to thickness ratio of at least 6:1 and preferably larger, such as greater than 30:1.

If the temperature of the media 11 in which the probe 20 may be immersed can vary, then it is desirable to measure the ambient temperature of the media 11. The self heated thermistor 30 may then be heated to a predetermined target temperature relative to the ambient temperature of the media 11. The actual temperature to which the self heated thermistor 30 is heated above the ambient temperature would be dependent upon the fluids 11 to which the probe 20 is likely to be exposed such that effective differentiation between the different types of media 11 may be accurately determined without having to use excessive electrical power to heat the self heated thermistor 30. For example, when using the detector 10 to differentiate between air, oil, water and moving water it has been found that heating the self heated thermistor 30 to about 25° C. above the ambient temperature of the surrounding media 11 provides excellent differentiation between different types of media whilst only requiring a modest amount of electrical power.

Figure 4:
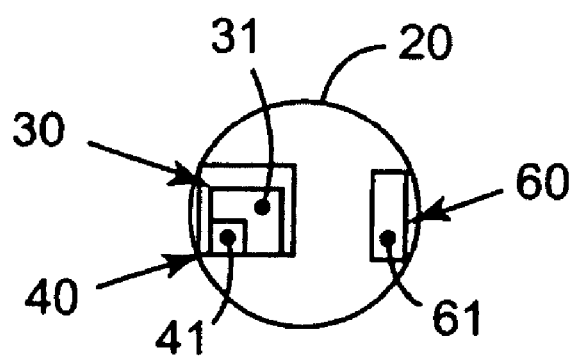
FIG. 4 shows a top view of the structure of a probe of another embodiment of the present invention.

FIG. 4 illustrates a top view of a detector 10 including an ambient temperature sensor 60 for measuring the ambient temperature of the media 11 to which the probe 20 is exposed. As can be seen, in this example the ambient temperature sensor 60 is spaced from the self heated thermistor 30 and feedback thermistor 40 to reduce any effects from the self heated thermistor 30 on the temperature measurements made by the ambient temperature sensor 60. A suitable thermal barrier may also be provided between the self heated thermistor 30 and the ambient temperature sensor 60 if required. Consequently, the ambient temperature sensor 60 is effectively thermally isolated from the self heated thermistor 30. As shown in FIG. 4, if there is likely to be any flow of the media 11 to which the probe 20 is exposed, the ambient temperature measuring sensor 60 is preferably provided upstream of the self heated thermistor 30 to further enhance the thermal isolation between the ambient temperature sensor 60 and the self heated thermistor 30. The ambient temperature sensor 60 may be provided by any suitable means, such as a further thermistor.

Figure 5:
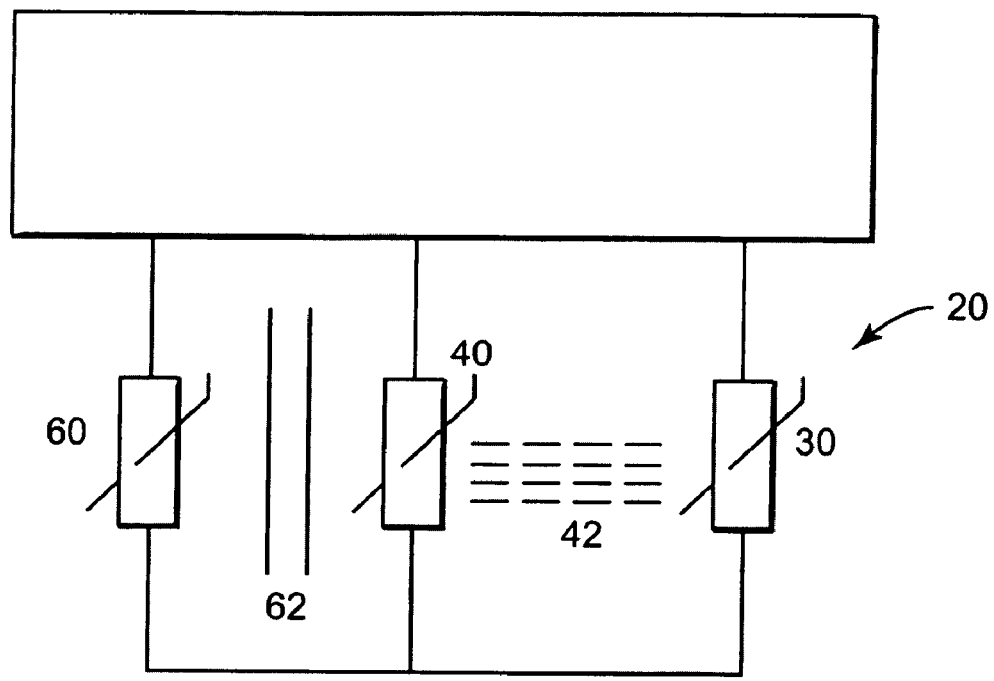
FIG. 5 illustrates an electrical circuit of an embodiment of the present invention.

FIG. 5 schematically illustrates a circuit providing the detector 10. The circuit includes the self heated thermistor 30 provided in good thermal contact 42 with the temperature measuring thermistor 40 which is thermally isolated 62 from the ambient temperature sensor 60. Each of the self heated thermistor 30 and temperature sensors 40, 60 is connected to the controller 50. The self heated thermistor 30 and temperature sensors 40, 60 are provided in the probe 20.

When the detector 10 is first turned on, the self heating thermistor 30 is supplied with electrical power from the controller 50 to heat it up to a predetermined temperature above the temperature measured by the ambient temperature sensor 60. The temperature of the self heated thermistor 30 is monitored by the temperature sensor 40 as indicated by step 100 of FIG. 6. When the self heated thermistor 30 reaches the predetermined target temperature above the ambient temperature of the media 11 measured by ambient temperature sensor 60, electrical power to the self heated thermistor 30 is turned off as indicated by step 110 of FIG. 6. When the temperature of the self heated thermistor 30 drops below the predetermined target temperature above the ambient temperature of the media 11, power is turned on again until the self heated thermistor 30 reaches the predetermined target temperature above the ambient temperature of the media 11 again as indicated by step 120 of FIG. 6. Thus the controller 50 enters a switching mode repeatedly turning electrical power to the self heated thermistor 30 on and off. Analysis of the overall proportion of time that power is supplied to the self heated thermistor 30 is then used to determine the presence and/or nature of the media 11 to which the self heated thermistor 30 is exposed as indicated by step 130 of FIG. 6. The proportion of time that the controller 50 supplies power to the self heated thermistor 30 or duty cycle is provided to a memory, look-up table or analogue means from which the presence and/or nature of the media 11 is determined.

The presence and/or nature of the media 11 may be indicated to a user in any suitable way, such as by illumination of an appropriate LED or the display on a display means (not shown) attached to the controller 50.

Figure 6:
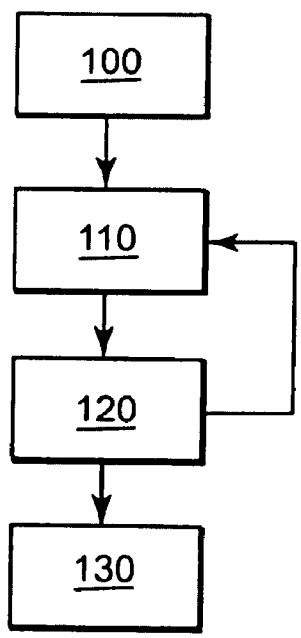
FIG. 6 is a flow chart illustrating operation of a detector according to an embodiment of the present invention.
Figure 7:
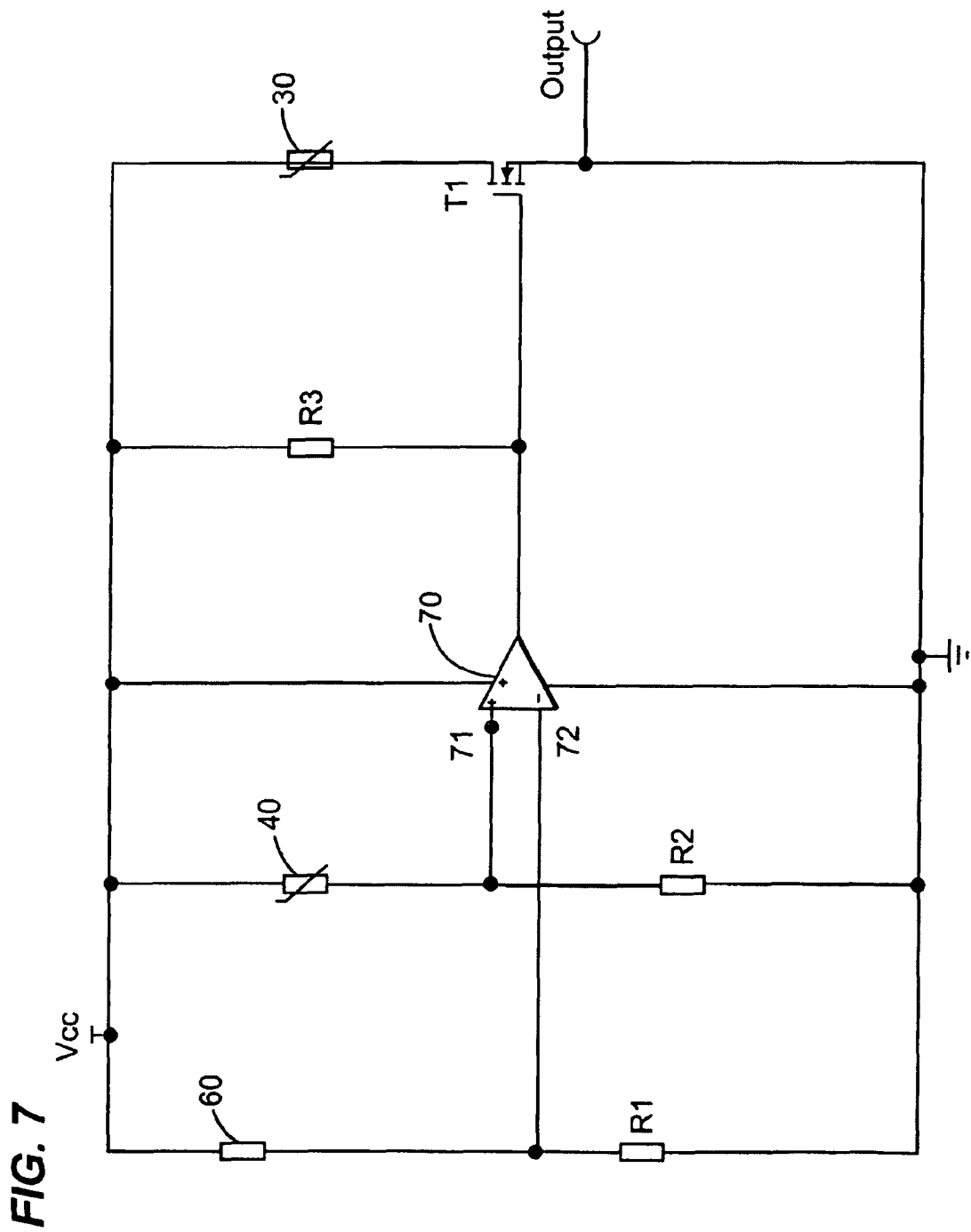
FIG. 7 shows a control circuit of another embodiment of the present invention.

FIG. 6 illustrates a more detailed example of an electrical circuit of a detector 10. An integrated circuit 70 acting as a comparator has a first input 71 based on the feedback thermistor 40 indicative of the temperature of the self heated thermistor and a second input 72 including the ambient temperature sensor 60. During operation, if the self heated thermistor 30 drops below the predetermined temperature above ambient, the resistance of the feedback thermistor 40 increases and the output of the comparator is changed from low to high. When the output of the comparator 70 goes high this turns on transistor T1 and electrical power is then supplied to self heated thermistor 30 to increase its temperature. Conversely, when the temperature of the feedback thermistor 40 reaches the predetermined target temperature, the output of the comparator 70 changes from high to low turning off transistor T1 such that electrical power to the self heated thermistor 30 is turned off.

Detection and monitoring of the on/off times of the self heated thermistor 30 are then used to determine the presence and/or nature of the media 11 exposed to the probe 20. Detection and monitoring of the on/off time of the self heated thermistor 30 may be performed in any suitable manner as is well known to the person skilled in the art, such as by using an associated RMS DC convertor.

As electrical power to the self heated thermistor 30 is constantly turned on and off, overall power consumption is reduced as compared to conventional arrangements.

Many variations may be made to the examples described above while still falling within the scope of the invention. For example, any suitable controller or electronic circuit may be used to detect and monitor the proportion of time that electrical power is supplied to the self heated thermistor 30. Furthermore, the present invention may be used with or without the ambient temperature sensor 60 depending upon the nature of the media in which the detector is to be used.

The invention claimed is:

1. A detector for determining the presence of a fluid, the detector comprising:
    a probe having a thermistor, the probe being arranged to be exposed to the fluid and to allow thermal flow between the thermistor and the fluid;
    a first temperature sensor for measuring the temperature of the thermistor;
    a controller for supplying electrical power to the thermistor when it is below a predetermined temperature to heat it up and to turn off the supply of electrical power to the thermistor when it is at or above the predetermined temperature, and to determine the presence of the fluid exposed to the probe in accordance with the proportion of time that power is supplied to the thermistor to maintain it substantially at the predetermined temperature;
    wherein the controller is arranged to identify the fluid based on the proportion of time that power is supplied to the thermistor to maintain it substantially at the predetermined temperature; and
    wherein the controller has a memory including data correlating different types of fluids to different proportions of time that power is supplied to the thermistor to maintain it substantially at the predetermined temperature.

2. A detector according to claim 1, wherein the controller includes two associated modules, one for supplying electrical power to the thermistor and one for determining at least one of the presence of the fluid and the identity of the fluid.

3. A detector according to claim 1, wherein the thermistor consists essentially of a metallised ceramic.

4. A detector according to claim 1, wherein a metallised ceramic layer is provided between the thermistor and the outer surface of the probe.

5. A detector according to claim 1, including a second temperature sensor to measure the ambient temperature of the fluid and wherein the controller is arranged to supply electrical power to the thermistor to maintain it substantially at a predetermined temperature above the measured ambient temperature of the fluid.

6. A detector according to claim 5, wherein the second ambient temperature sensor is thermally isolated from the heated thermistor.

7. A method for determining the presence of a fluid, the method comprising:
    exposing a probe including a thermistor to a fluid to provide thermal flow between the thermistor and the fluid;
    measuring the temperature of the thermistor;
    controlling a supply of electrical power to the thermistor to keep it substantially at a predetermined temperature by supplying electrical power to the thermistor when it is below a predetermined temperature to heat it up and turning off the supply of electrical power to the thermistor when it is at or above the predetermined temperature; and
    determining the presence of the fluid in contact with the probe in accordance with the proportion of time that electrical power is supplied to the thermistor, wherein the identity of the fluid is determined in accordance with the proportion of time that power is supplied to the thermistor to keep it substantially at a predetermined temperature.

8. A method in accordance with claim 7, further comprising:
    measuring the ambient temperature of the fluid; and supplying electrical power to the thermistor to keep it substantially at a predetermined temperature above the measured ambient temperature.

* * * * *